US008066779B2

(12) United States Patent
Gibbs et al.

(10) Patent No.: US 8,066,779 B2
(45) Date of Patent: *Nov. 29, 2011

(54) MODULAR HIP JOINT IMPLANT

(75) Inventors: Phillip M. Gibbs, Winona Lake, IN (US); Monty J. Lackey, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 17 days.

This patent is subject to a terminal disclaimer.

(21) Appl. No.: 12/644,920

(22) Filed: Dec. 22, 2009

(65) Prior Publication Data

US 2010/0114324 A1    May 6, 2010

Related U.S. Application Data

(62) Division of application No. 10/862,150, filed on Jun. 4, 2004, now Pat. No. 7,641,698.

(51) Int. Cl.
*A61F 2/32* (2006.01)
(52) U.S. Cl. .................. 623/22.42; 623/22.4; 623/22.41
(58) Field of Classification Search ...... 623/22.4–22.46; A61F 2/32
See application file for complete search history.

(56) References Cited

U.S. PATENT DOCUMENTS

| | | | |
|---|---|---|---|
| 1,807,646 A | 6/1931 | Wright | |
| 3,671,978 A | 6/1972 | May | |
| 3,815,590 A | 6/1974 | Deyerle | |
| 4,090,796 A | 5/1978 | Okuda et al. | |
| 4,153,953 A | 5/1979 | Grobbelaar | |
| 4,306,550 A | 12/1981 | Forte | |
| D272,648 S | 2/1984 | Bolesky et al. | |
| D273,806 S | 5/1984 | Bolesky et al. | |
| 4,552,136 A | 11/1985 | Kenna | |
| 4,578,081 A | 3/1986 | Harder et al. | |
| D284,100 S | 6/1986 | Kenna | |
| 4,601,289 A | 7/1986 | Chiarizzio et al. | |
| 4,605,416 A | 8/1986 | Grobbelaar | |
| 4,667,664 A | 5/1987 | Taylor et al. | |
| 4,710,075 A | 12/1987 | Davison | |
| 4,790,854 A | 12/1988 | Harder et al. | |
| 4,795,473 A | 1/1989 | Grimes | |
| 4,822,370 A | 4/1989 | Schelhas | |
| 4,865,609 A | 9/1989 | Roche | |
| 4,921,493 A | 5/1990 | Webb, Jr. et al. | |
| 4,923,472 A | 5/1990 | Ugolini | |
| 4,963,155 A | 10/1990 | Lazzeri et al. | |
| 5,002,581 A | 3/1991 | Paxson et al. | |
| 5,019,108 A | 5/1991 | Bertin et al. | |
| 5,041,118 A | 8/1991 | Wasilewski | |
| 5,080,685 A | 1/1992 | Bolesky et al. | |
| 5,087,260 A | 2/1992 | Fixel | |
| 5,089,004 A | 2/1992 | Averill et al. | |

(Continued)

OTHER PUBLICATIONS

"Alliance® Hip Systems," brochure, Biomet, Inc. (17 sheets).

(Continued)

*Primary Examiner* — Thomas J Sweet
*Assistant Examiner* — Jason-Dennis Stewart
(74) *Attorney, Agent, or Firm* — Harness, Dickey

(57) ABSTRACT

A modular hip joint implant and associated method. The modular hip implant includes a femoral stem having a proximal surface defining a dovetail groove having first and second female wings, and a neck component having a distal surface defining a semi-dovetail projection engaging the dovetail groove. The projection includes a single male wing mating with the first femoral wing.

20 Claims, 11 Drawing Sheets

U.S. PATENT DOCUMENTS

| | | |
|---|---|---|
| 5,108,451 A | 4/1992 | Forte |
| 5,116,379 A | 5/1992 | McLardy-Smith |
| 5,156,627 A | 10/1992 | Amstutz et al. |
| 5,181,928 A | 1/1993 | Bolesky et al. |
| 5,201,769 A | 4/1993 | Schutzer |
| 5,286,260 A | 2/1994 | Bolesky et al. |
| 5,314,479 A | 5/1994 | Rockwood, Jr. et al. |
| 5,342,366 A | 8/1994 | Whiteside et al. |
| 5,358,526 A | 10/1994 | Tornier |
| 5,370,706 A | 12/1994 | Bolesky et al. |
| 5,403,320 A | 4/1995 | Luman et al. |
| 5,458,654 A | 10/1995 | Tepic |
| 5,507,818 A | 4/1996 | McLaughlin |
| 5,507,830 A | 4/1996 | DeMane et al. |
| 5,549,706 A | 8/1996 | McCarthy |
| 5,601,567 A | 2/1997 | Swajger et al. |
| 5,607,431 A | 3/1997 | Dudasik et al. |
| 5,653,765 A | 8/1997 | McTighe et al. |
| 5,658,352 A | 8/1997 | Draenert |
| 5,704,940 A | 1/1998 | Garosi |
| 5,728,161 A | 3/1998 | Camino et al. |
| 5,766,174 A | 6/1998 | Perry |
| 5,766,261 A | 6/1998 | Neal et al. |
| 5,800,553 A | 9/1998 | Albrektsson et al. |
| 5,800,560 A | 9/1998 | Draenert |
| 5,860,969 A | 1/1999 | White et al. |
| 5,860,982 A | 1/1999 | Ro et al. |
| 5,885,295 A | 3/1999 | McDaniel et al. |
| 5,888,208 A | 3/1999 | Ro |
| 5,906,644 A | 5/1999 | Powell |
| 5,908,423 A | 6/1999 | Kashuba et al. |
| 5,931,841 A | 8/1999 | Ralph |
| 5,976,145 A | 11/1999 | Kennefick, III |
| 5,993,455 A | 11/1999 | Noble |
| 6,083,263 A | 7/2000 | Draenert et al. |
| 6,106,528 A | 8/2000 | Durham et al. |
| 6,117,138 A | 9/2000 | Burrows et al. |
| 6,120,504 A | 9/2000 | Brumback et al. |
| 6,129,764 A | 10/2000 | Servidio |
| 6,168,627 B1 | 1/2001 | Huebner |
| 6,179,877 B1 | 1/2001 | Burke |
| 6,193,758 B1 | 2/2001 | Huebner |
| 6,193,759 B1 | 2/2001 | Ro et al. |
| 6,238,436 B1 | 5/2001 | Lob et al. |
| 6,264,699 B1 | 7/2001 | Noiles et al. |
| 6,299,648 B1 | 10/2001 | Doubler et al. |
| 6,306,174 B1 | 10/2001 | Gie et al. |
| 6,338,734 B1 | 1/2002 | Burke et al. |
| 6,355,068 B1 | 3/2002 | Doubler et al. |
| 6,383,225 B2 | 5/2002 | Masini |
| 6,440,171 B1 | 8/2002 | Doubler et al. |
| 6,613,092 B1 | 9/2003 | Kana et al. |
| 7,179,259 B1 | 2/2007 | Gibbs |
| 7,235,101 B2 | 6/2007 | Berry et al. |
| 7,641,698 B1 | 1/2010 | Gibbs et al. |
| 2002/0040244 A1 | 4/2002 | Despres et al. |
| 2002/0072802 A1* | 6/2002 | O'Neil et al. ............... 623/20.33 |
| 2002/0099447 A1 | 7/2002 | Mears et al. |
| 2002/0116067 A1 | 8/2002 | Mears et al. |
| 2002/0120343 A1 | 8/2002 | Doubler et al. |
| 2002/0128720 A1 | 9/2002 | Masini |
| 2003/0028198 A1 | 2/2003 | Tornier et al. |
| 2003/0135211 A1 | 7/2003 | Cho |
| 2003/0158606 A1 | 8/2003 | Coon et al. |
| 2003/0204268 A1 | 10/2003 | Gerbec et al. |
| 2003/0204269 A1 | 10/2003 | Gerbec et al. |
| 2003/0220698 A1 | 11/2003 | Mears et al. |
| 2003/0222470 A1 | 12/2003 | Alba et al. |
| 2004/0064186 A1 | 4/2004 | McCleary et al. |
| 2005/0143834 A1* | 6/2005 | Lester et al. ................. 623/22.4 |

OTHER PUBLICATIONS

"Answer® Hip System Surgical Technique," brochure Biomet Orthopedics, Inc. Copyright 2001 (11 sheets).

"Impact Modular™ Total Hip System," brochure, Biomet, Inc., Copyright 1992.

"Mallory-Head Radial™ Acetabular Shell," brochure Biomet, Inc. Copyright 1998 (2 sheets).

"Osteocap RS™ Hip System Surgical Technique," brochure, Biomet Orthopedics, Inc. Copyright 2001 (12 sheets).

"Stanmore™ Modular Hip System," brochure, Biomet, Inc. Copyright 1998 (12 sheets).

"Taperloc® Hip System," brochure, Biomet, Inc. Copyright 2000 (13 sheets).

* cited by examiner

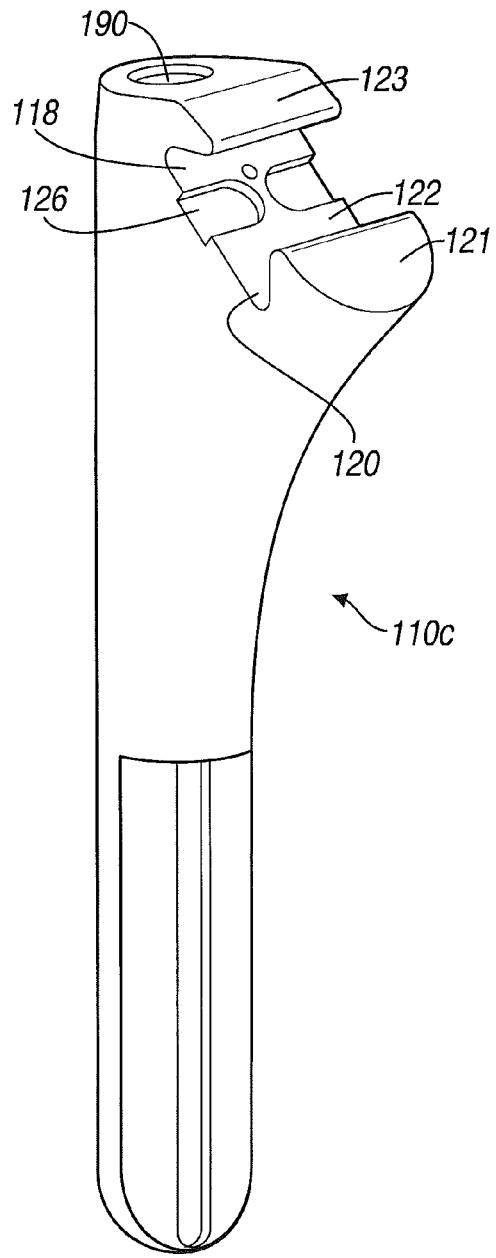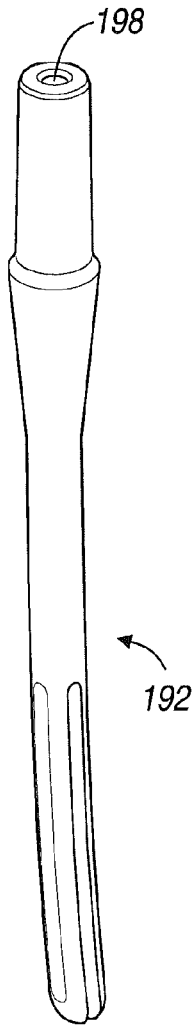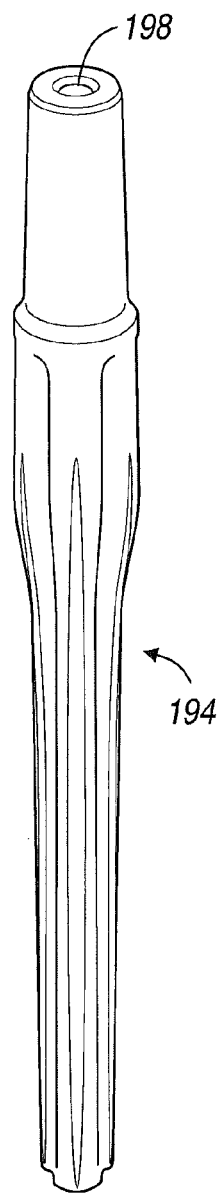
FIG. 4A
FIG. 4B
FIG. 4C

MODULAR HIP JOINT IMPLANT

CROSS-REFERENCE TO RELATED APPLICATIONS

This application is a divisional application of U.S. patent application Ser. No. 10/862,150, filed on Jun. 4, 2004. The entire disclosure of the above application is incorporated herein by reference in its entirety.

INTRODUCTION

Modular prosthetic devices can be used in total or revision hip procedures. Modularity has the advantage of added flexibility and choice, enabling the practicing surgeon to select appropriately sized interconnected components for specific conditions and patients. Nevertheless, some of the available modular components can still be bulky or cumbersome for implantation with current minimally invasive procedures, which require small-sized incisions.

Accordingly, improved modular hip joint implants are still desirable.

SUMMARY

The present teachings provide in various embodiments a modular hip joint implant. The modular hip implant can include a femoral stem having a proximal surface defining a dovetail groove having first and second female wings, and a neck component having a distal surface defining a semi-dovetail projection engaging the dovetail groove. The projection can include a single male wing mating with the first femoral wing.

The present teachings also provide a modular hip joint implant that includes a femoral stem and a neck component. The femoral stem has a proximal surface that defines a dovetail groove with first and second female wings. The neck component has a distal surface that defines a semi-dovetail projection having a single male wing. The semi-dovetail projection slidably interlocks with the dovetail groove such that a keyway is defined between the second female wing and the neck component. The implant can include a key wedgeable in the keyway to lock the femoral stem and the neck component against relative sliding.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4A is a perspective view of an exemplary non-collared stem according to the present teachings;

FIG. 4B is a perspective view of an exemplary stem extension according to the present teachings;

FIG. 4C is a perspective view of an exemplary stem extension according to the present teachings;

DESCRIPTION OF VARIOUS EMBODIMENTS

Figure 1:
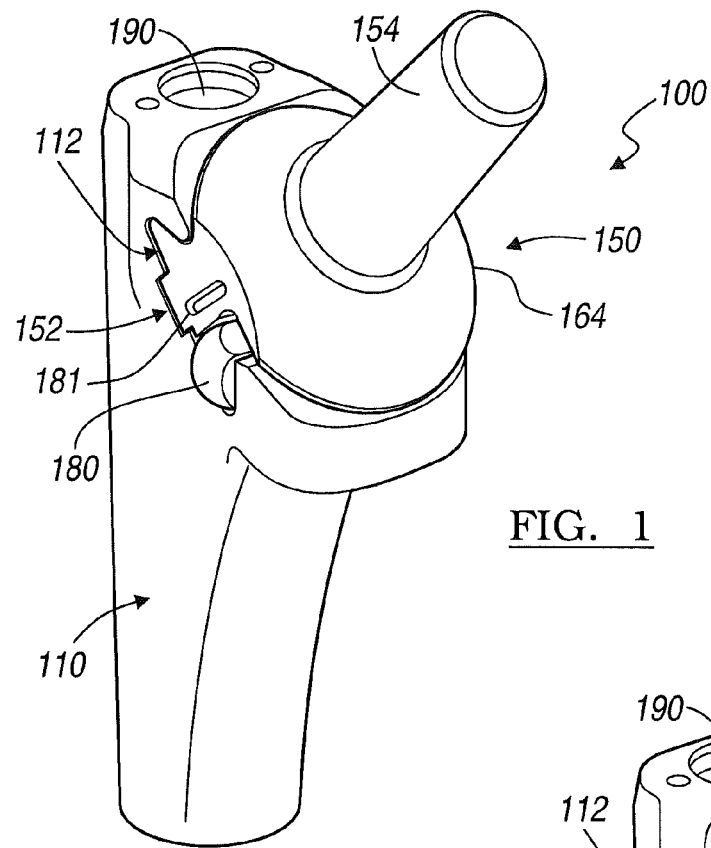
FIG. 1 is a perspective view of a modular hip joint implant according to the present teachings.
Figure 2:
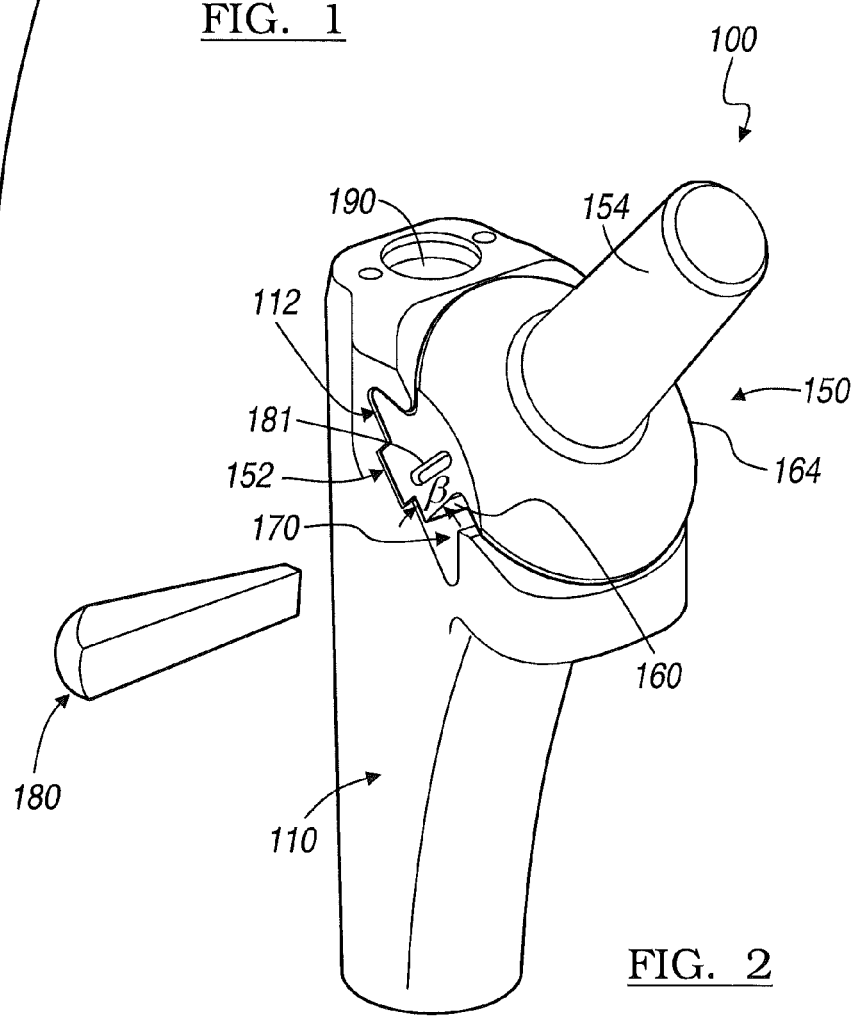
FIG. 2 is a partially exploded perspective view of a modular hip joint implant according to the present teachings.
Figure 8:
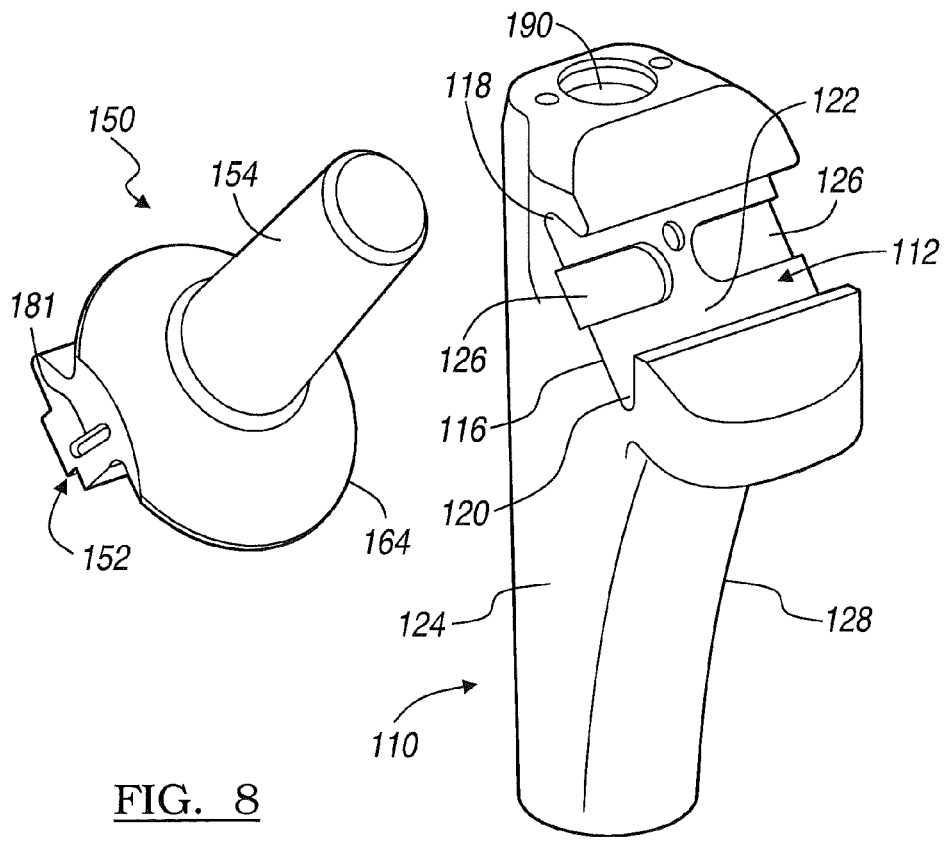
FIG. 8 is a partially exploded perspective view of a modular hip joint implant according to the present teachings.
Figure 9:
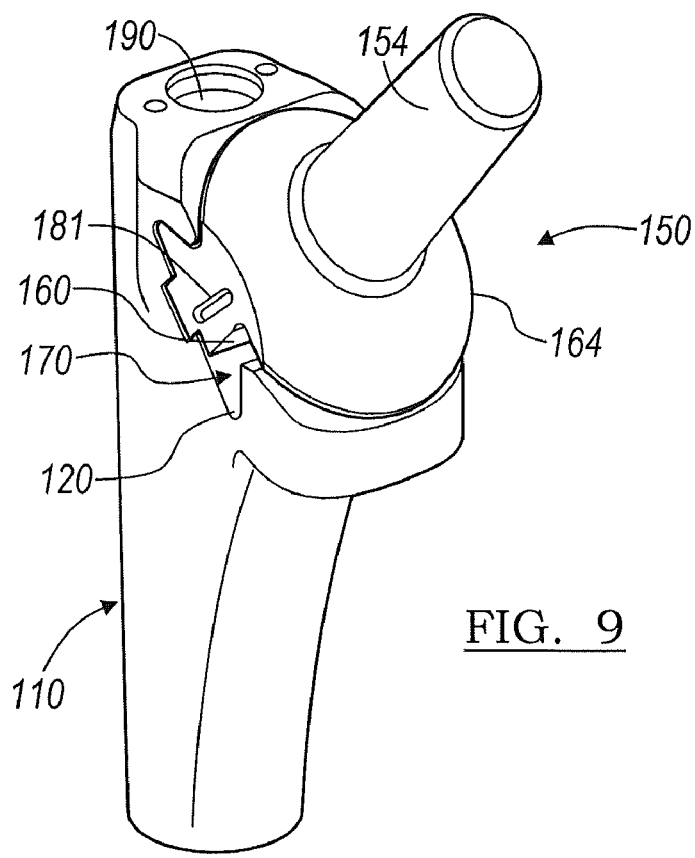
FIG. 9 is a perspective view of a modular hip joint implant according to the present teachings.
Figure 13:
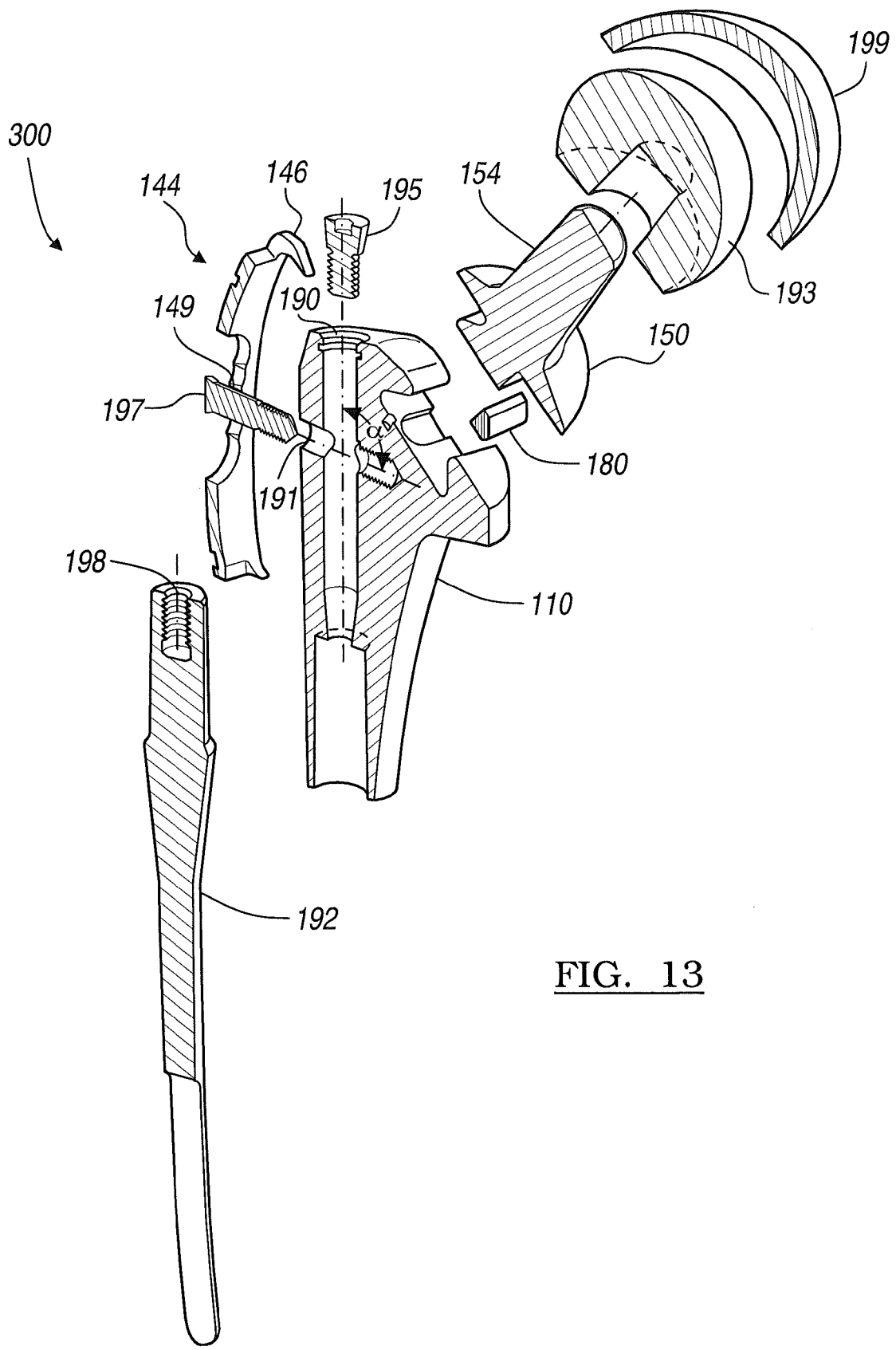
FIG. 13 is an exploded view of a modular hip replacement system according to the present teachings.
Figure 14:
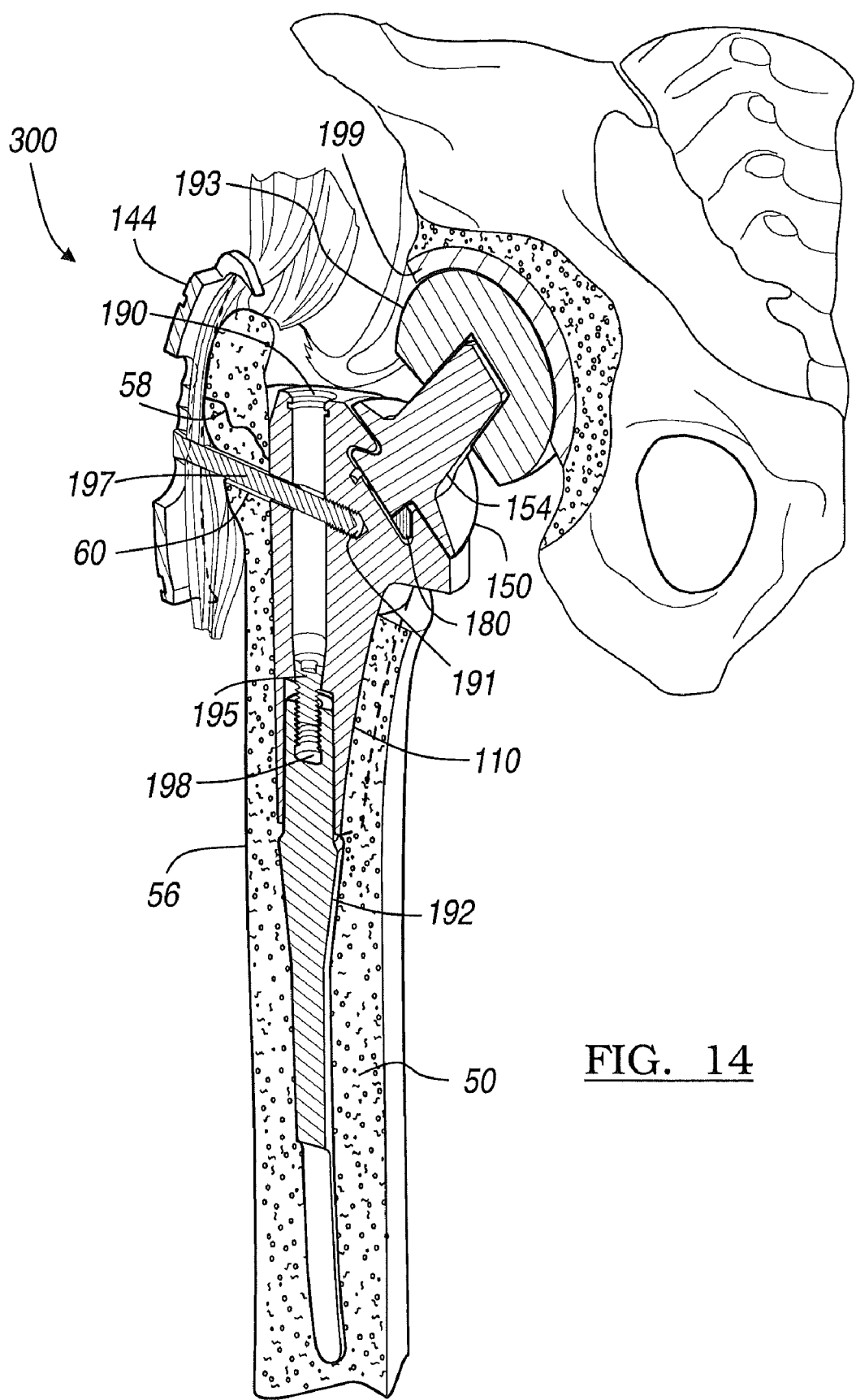
FIG. 14 is an environmental sectional view of a modular hip replacement system.
Figure 15:
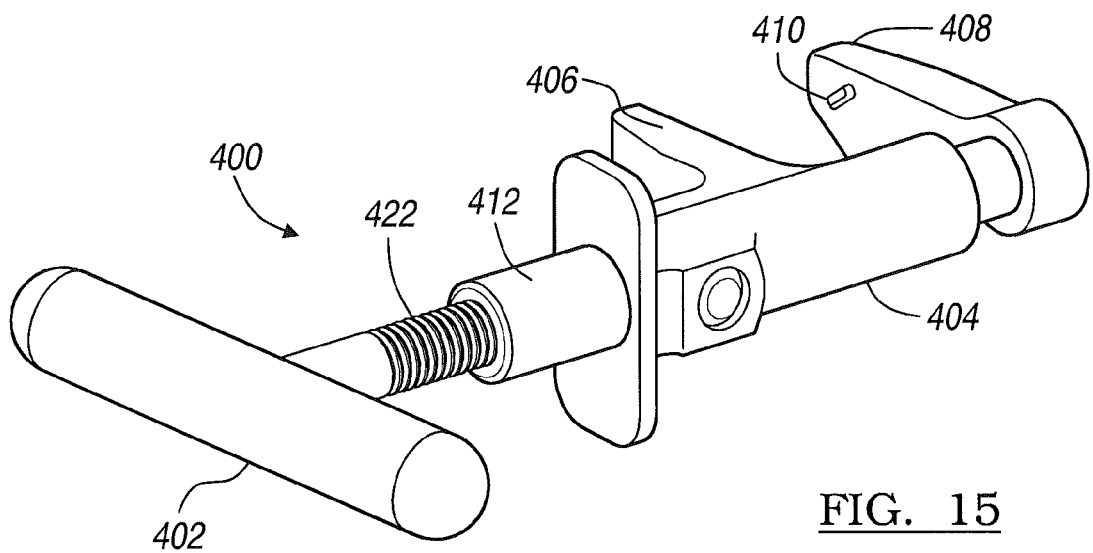
FIG. 15 is a perspective view of an installation tool according to the present teachings.
Figure 16:
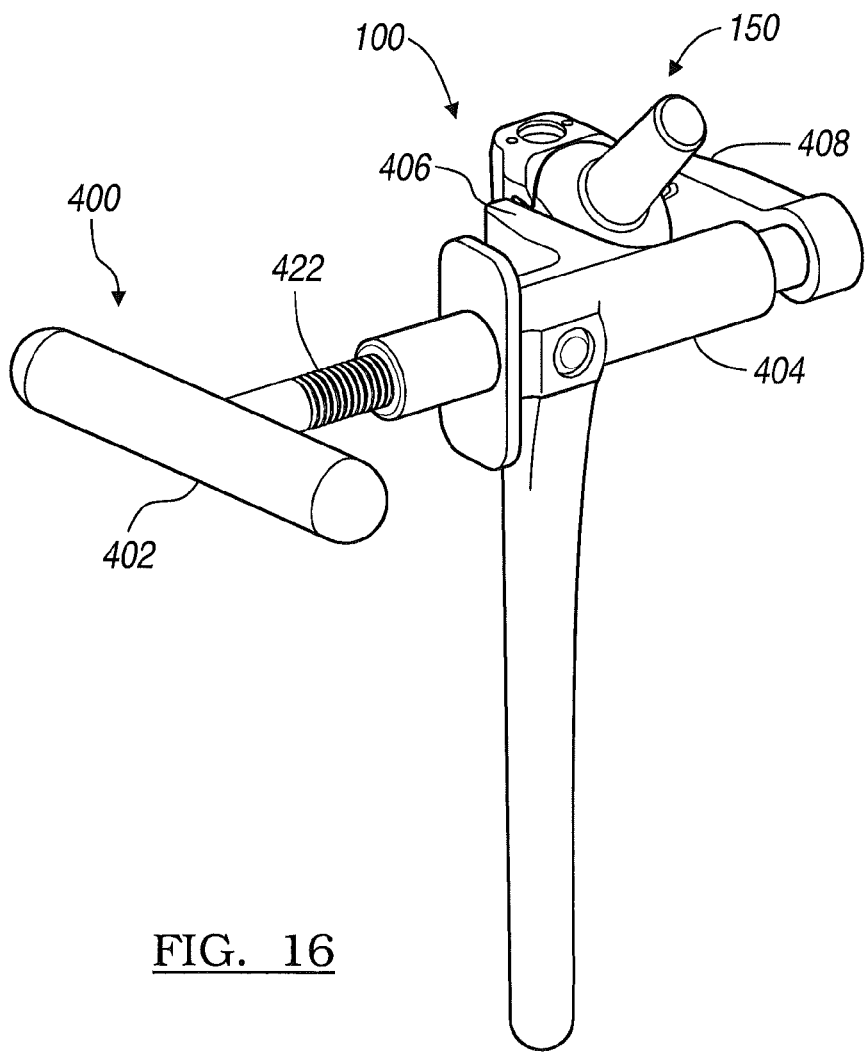
FIG. 16 is a perspective view of the installation tool of FIG. 15 shown in use with a modular hip implant according to the present teachings.

The following description of various embodiments is merely exemplary in nature and is in no way intended to limit the invention, its application, or uses. For example, although the invention is illustrated for a hip implant, the invention can be used with any type of prosthesis for a bone such as, for example, a proximal or distal femur, a proximal or distal tibia, a pro FIGS. 1, 13 and 14 illustrate respectively an exemplary of a modular hip joint implant 100 and an exemplary modular hip replacement system 300. The implant 100 includes a femoral stem 110, a neck component 150, and a key 180. The femoral stem 110 and the neck component 150 have opposing interlocking proximal stem and distal neck surfaces 112, 152, which allow for relative sliding therebetween, as best seen in FIGS. 8 and 9. When interlocked, the femoral stem 110 and neck component 150 define a keyway 170. The key 180 can be wedged into the keyway 170 to lock the components of the modular hip joint implant 100 together and substantially prevent relative motion between the femoral stem 110 and the neck component 150. It should be appreciated that interlocking does not require complete contact along the entire surfaces 112, 152, such that a small gap could be defined between portions thereof, as best seen in FIGS. 1 and 2.

Figure 3:
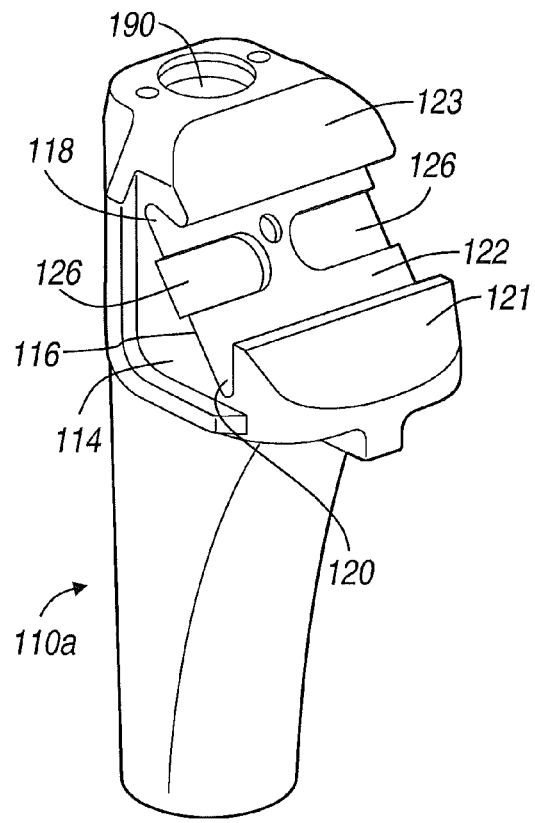
FIG. 3 is a perspective view of an exemplary calcar stem according to the present teachings.
Figure 4:
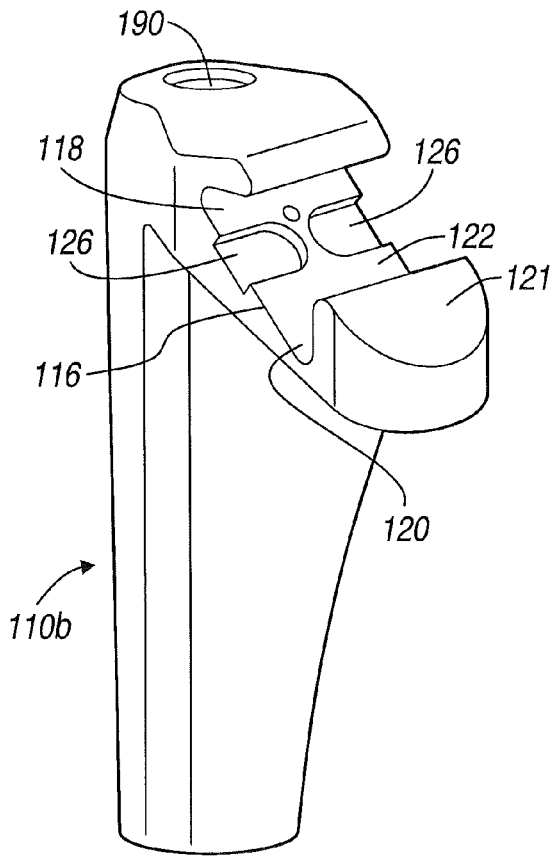
FIG. 4 is a perspective view of an exemplary collared stem according to the present teachings.

The femoral stem 110 can be a primary stem or a revision stem implantable in a femur 50. It can also be a calcar stem 110a having a calcar portion 114, as illustrated in FIG. 3, an ordinary collared stem 110b, as illustrated in FIG. 4, or a non-collared stem 110c, as illustrated in FIG. 4A. The calcar stem 110a is appropriate when the calcar region of the femur is weak, porotic, or otherwise defective, and needs strengthening. The size of the calcar portion 114 of the femoral stem 110a depends on the degree of defectiveness or need for reinforcement of the calcar region of the femur. The term "femoral stem 110" will be understood to include the calcar stem 110a, the collared stem 110b, the non-collared stem 110c, and any variations/combinations thereof. The femoral stem 110 includes two planar portions 121, 123, the size of which depends on the type of stem being used, as seen in FIGS. 3, 4 and 4A. Furthermore, and in reference to FIGS. 4A, 4B, 4C, 13, and 14 the femoral stem 110 can be one integral piece, or can be modular, with stem extensions 192, 194, which can be coupled to the femoral stem 110 with Morse taper connections and locked in place with locking screws or other fasteners 195, which can be inserted, for example, through bores 190 of the femoral stems 110 to engage respective bores 198 of the stem extensions 192, 194. As shown in FIGS. 4B and 4C, it will be appreciated that the stem extensions can be distally slotted, fluted or non-fluted, can have different diameters and lengths, and different lengths of porous coatings.

Referring to FIGS. 13 and 14, the femoral stem 110 can be additionally attached to the trochanter of the femur 50 with a lateral fastener 197, such as, for example, a trochanteric bolt, which is threaded to the femoral stem 110 through a blind bore 191 transverse or at an angle to the longitudinal bore 190. The lateral fastener 197 is inserted into the lateral blind bore 191 from the lateral side 56 of the femur 50 through a lateral hole 60 drilled into the bone 50. The lateral hole 60 is coaxial with the lateral blind bore 191 of the stem body 102. The lateral fastener 197 can also retain a lateral support or claw plate 144, which is implanted laterally in soft tissue adjacent to the lateral side 56 of the femur 50 for reinforcement or for providing support for a bone fragment 58, such as a portion of a trochanter, broken off or resected from the lateral side 56 of the femur 50. The lateral support plate 144 is retained in position by the head 148 of the lateral fastener 197, with the head 148 received in a countersunk bore 149 of the support plate 144. The support plate 144 can have a variety of shapes depending on the particular application and can also be anatomically configured, having a shape that conforms to the shape of the lateral side 56 of the femur 50 or the bone fragment 58. The support plate 144 can also include anchors 146 for soft tissue attachment.

With continued reference to FIGS. 3 and 4, the interlocking proximal stem surface 112 defines a dovetail groove 116 on the femoral stem 110. The dovetail groove 116 includes first and second female extensions or "wings" 118, 120 and a base surface 122. Although the wings 118, 120 are illustrated as two-sided end grooves, it should be appreciated that the wings 118, 120 could have other shapes, such as, for example, polygonal, rectangular, arcuate or otherwise curved. Additionally, one or two slots 126 can be provided on the base surface 122. Each slot 126 extends from a midsection of the base surface 122 to an anterior surface 124 or posterior surface 128 of the femoral stem 110, and functions to guide the neck component 150 for insertion from the anterior or the posterior direction respectively.

Figure 5:
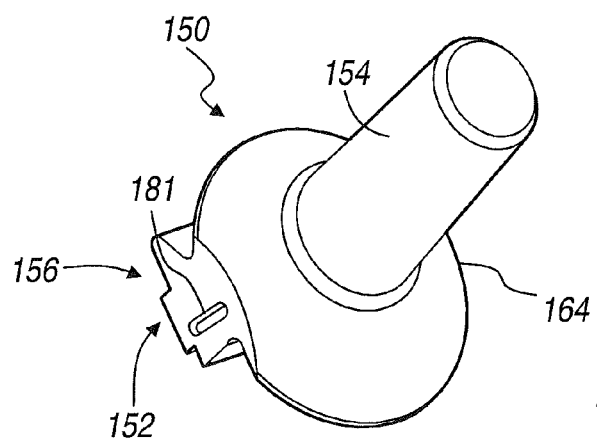
FIG. 5 is a top perspective view of an exemplary neck component according to the present teachings.
Figure 6:
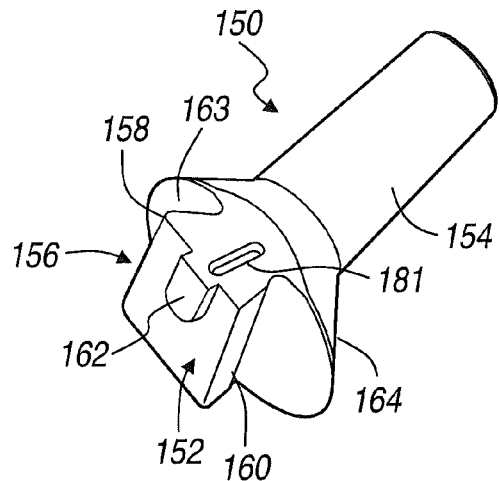
FIG. 6 is a bottom perspective view of the neck component of FIG. 5.

Referring to FIGS. 5, 6, and 13, the neck component 150 includes a trunnion 154 for connection to a femoral head 193, and a semi-dovetail projection 156, which is defined on the distal neck surface 152. The femoral head 193 can be attached to the trunnion 154 by a Morse taper connection, for example.

An acetabular cup 199 can be provided for articulation with the femoral head 193. The projection 156 integrally includes a single (first) male wing 158, which is adapted to conform with the first female wing 118 of the dovetail groove 116 of the femoral stem 110. On the opposite side of the male wing 158, the projection 156 terminates at a planar surface 160, completely lacking an integral second male wing or at most has an incomplete male wing, such that when the dovetail projection 156 mates with the dovetail groove 116, the second female wing 120 remains empty. The projection 156 can also include a keel 162 which is shaped to be nestingly received in the posterior or anterior slot 126 of the femoral stem 110, slidably guiding the neck component 150 in engagement with the femoral stem 110. With reference to FIG. 6, the neck component 150 includes a flange portion 164 having a lower surface 163. The lower surface 163 engages the planar portions 121, 123 of the femoral stem 110, when the femoral stem 110 and the neck component 150 are interlocked. It will be appreciated that the locations of the dovetail groove 116 and the dovetail projection 156 can be reversed, such that the dovetail groove 116 is defined on the neck component 150 and the dovetail projection 156 is defined on the femoral stem 110.

Figure 10:
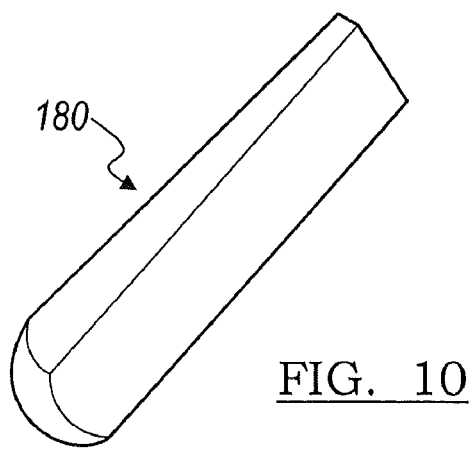
FIG. 10 is a right perspective view of a key for a modular hip joint implant according to the present teachings.
Figure 11:
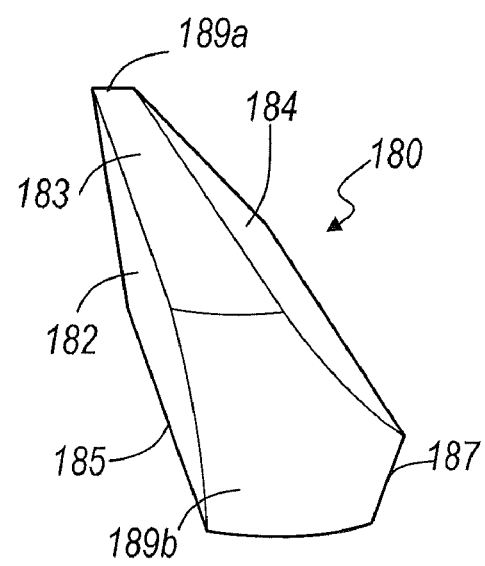
FIG. 11 is a top perspective view of a key for a modular hip joint implant according to the present teachings.

Referring to FIGS. 1 and 2, the key 180 is inserted in the keyway 170, locking the femoral stem 110 to the neck component 150 and preventing relative sliding. As best seen in FIGS. 10 and 11, the key 180 is configured to be wedged into the keyway 170. The key 180 completes the dovetail connection between the femoral stem 110 and the neck component 150 functioning as a second male wing that complements the first male wing 158 of the projection 156 to complete a male dovetail projection. As best seen in FIGS. 10 and 11, the key 180 can be tapered along its length substantially from a first end 189a to a second end 189b, in the anterior-posterior direction, matching the tapered keyway 170. The key 180 can have a five-sided peripheral surface, including a first surface 182 that conforms with the surface 160 of the projection 156, a second surface 184 that conforms with a corresponding surface of the second female wing 120 of the dovetail groove 116, and a third surface 185 for contact with the base surface 122 of the dovetail groove 116. The key 180 can include two additional surfaces 183, 187 along its length, as shown in FIG. 11.

Referring to FIGS. 1 and 2, the key 180 is inserted in the keyway 170, locking the femoral stem 110 to the neck component 150 and preventing relative sliding. As best seen in FIGS. 10 and 11, the key 180 is configured to be wedged into the keyway 170. The key 180 completes the dovetail connection between the femoral stem 110 and the neck component 150 functioning as a second male wing that complements the first male wing 158 of the projection 156 to complete a male dovetail projection. As best seen in FIGS. 10 and 11, the key 180 can be tapered along its length, in the anterior-posterior direction, matching the tapered keyway 170. The key 180 has a first surface 182 that conforms with the surface 160 of the projection 156, a second surface 184 that conforms with a corresponding surface of the second female wing 120 of the dovetail groove 116, and a third surface 185 for contact with the base surface 122 of the dovetail groove 116.

The implant 100 can be made of biocompatible materials, such, for example, a Ti-6Al-4V, although other metals and alloys can also be used. The implant 100 may be used advantageously in minimally invasive surgery, and, for example, with a two-incision approach. The femoral stem 110 can be introduced into the femur through a small posterior incision, having length of about two inches, for example, and leading to a small tunnel within soft tissues. Once the femoral stem 110 is in place in the femur, the neck component 150 can be attached to the femoral stem 110 through a second small anterior incision, having length about two inches, for example. The dovetail junction makes it possible to slide the neck component 150 in place with the minimum of hip manipulation. It will be appreciated that incisions other than posterior and anterior, including a single incision, can be used for inserting the implant 100.

Figure 7:
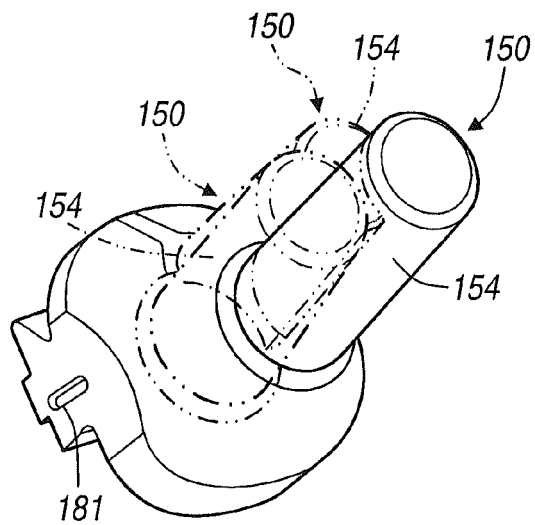
FIG. 7 is a superimposed perspective view of three exemplary neck components.

Several neck components 150 may be used with the implant 100. For example, various horizontal offsets, vertical offsets, anteversion and retroversion angles, neck lengths and angles can be offered. FIG. 7 illustrates three exemplary neck components overlaid to show three different positions of each trunnion 154 in each neck component 150, such as anterior, posterior and center positions. The posterior position is shown in solid lines, while the anterior and center positions are shown in phantom lines.

Figure 12:
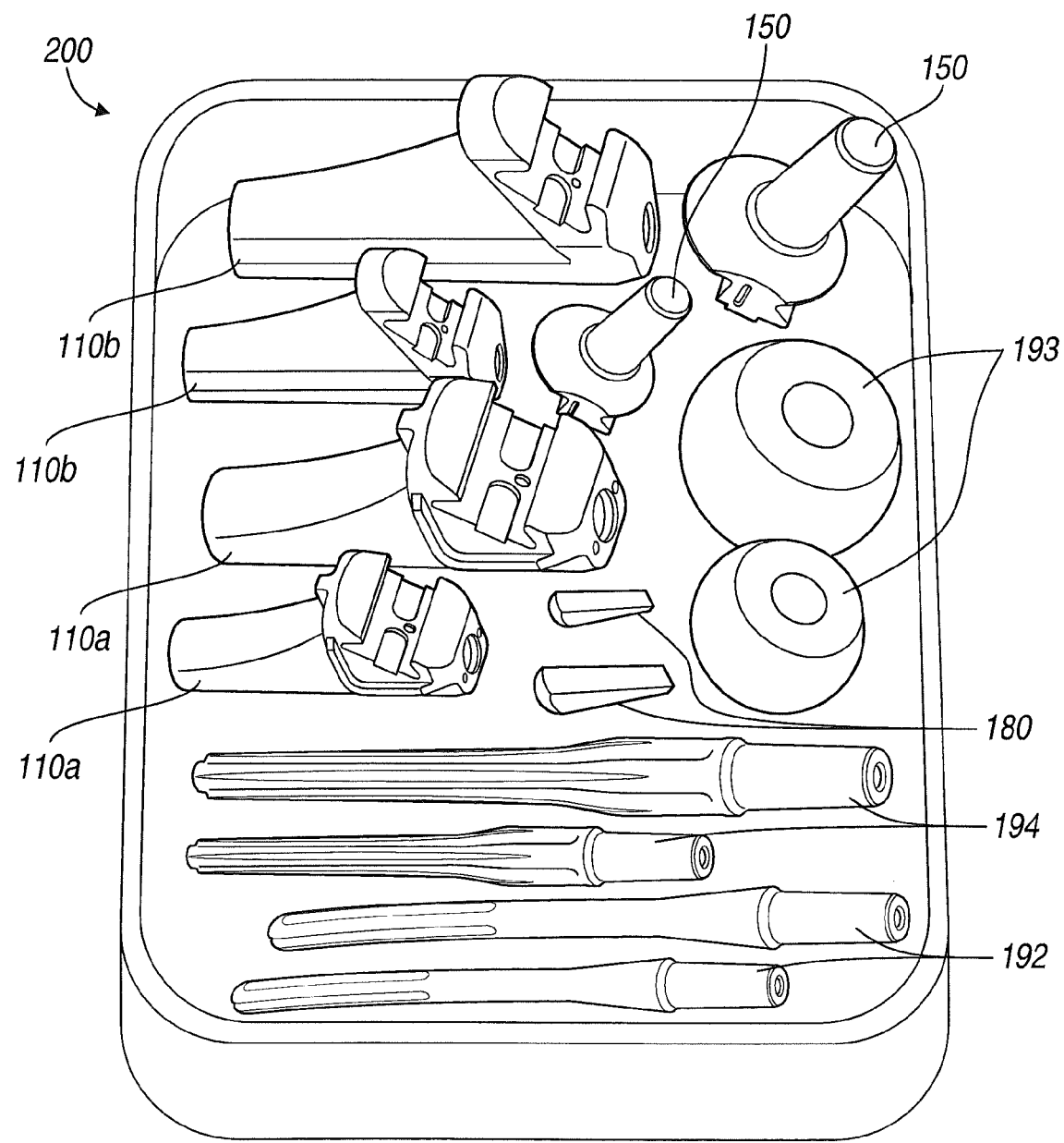
FIG. 12 is a kit of modular components according to the present teachings.

Referring to FIG. 12, a kit 200 of modular components of different sizes and shapes, such as femoral stems 110, stem extensions 192, 194, neck components 150, femoral heads 193, and keys 180 can be provided to aid the operating surgeon in selecting the appropriate size and orientation for each procedure. The kit 200 may also include acetabular cups 199 of different sizes (shown in FIG. 13).

Figure 17:
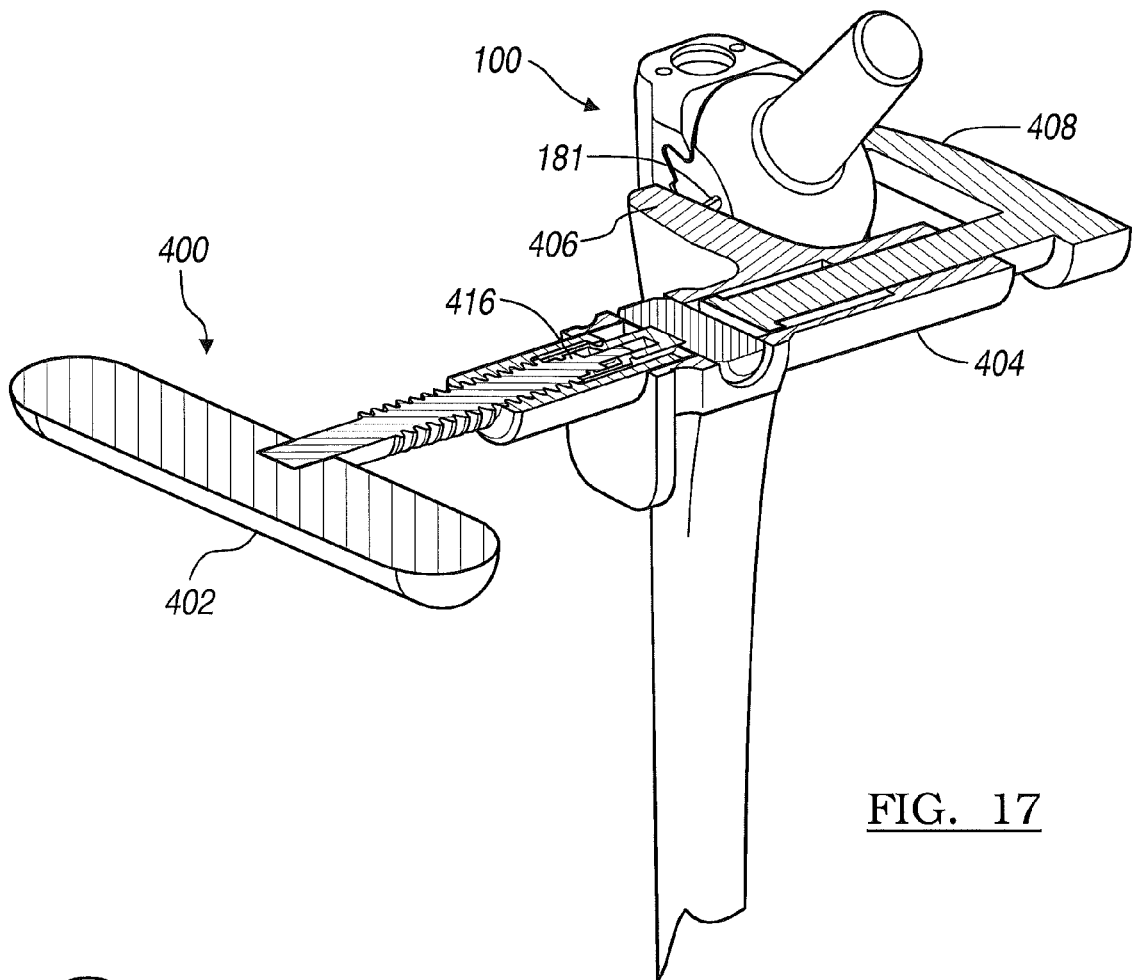
FIG. 17 is a cross-sectional view of the installation tool shown in FIG. 16.
Figure 18:
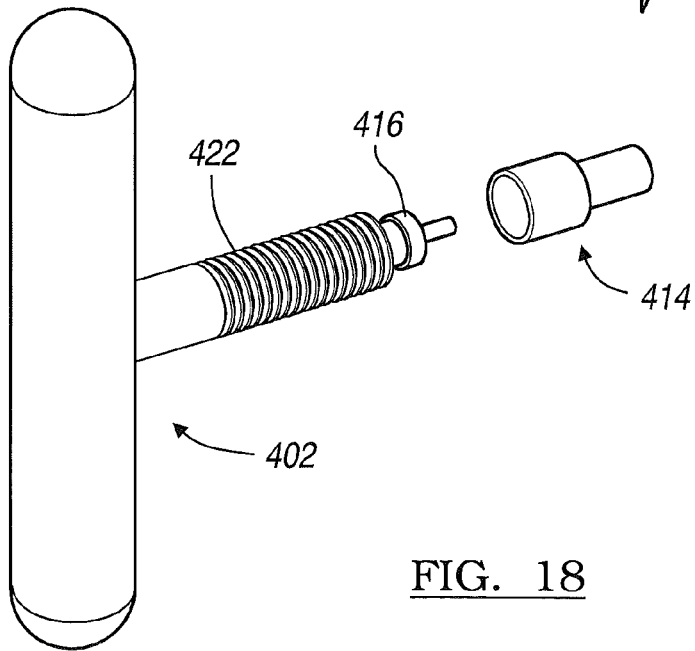
FIG. 18 is an exploded view of a portion of the installation tool of FIG. 15 illustrating a shear pin according to the present teachings.

Referring to FIGS. 15-20, an exemplary installation tool 400 for use with the modular hip implant 100 includes a T-shaped driver 402 and a body 404. The body 404 has a tubular extension 412 and first and second jaws 406, 408, which are spring loaded and biased towards a position that brings the first and second jaws 406, 408 toward each other. Referring to FIG. 18, the driver 402 includes an externally threaded portion 422 that can mesh with internal threading of the tubular extension 412 of the body 404. The driver 402 includes a friction ring 416.

Figure 19:
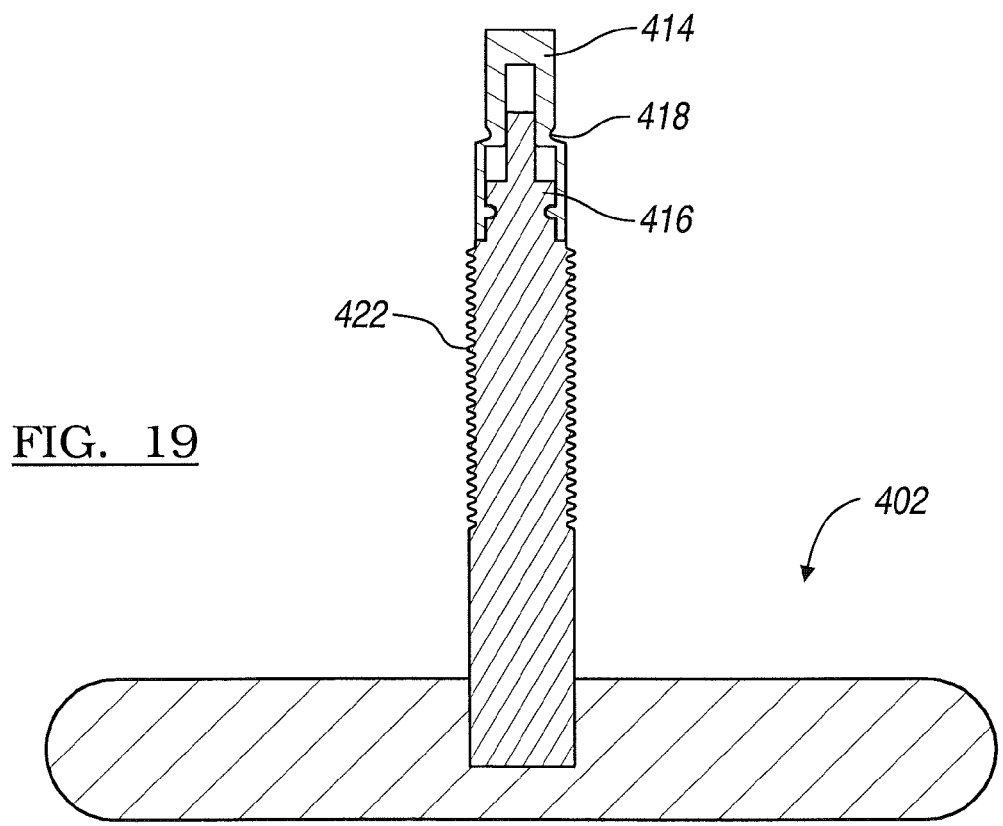
FIG. 19 is an assembled view of the portion of the installation tool shown in FIG. 18.

In use, the driver 402 is disconnected from the body 404, and a shear pin 414 is attached on the driver 402 against the friction ring 416. The driver 402 is then re-connected to the body 404 and the shear pin 414 is received into the tubular extension 412 of body 404. The tip of the driver 402, the ring 416, and the tubular extension 412 are configured to align the shear pin 414 axially to provide consistent axial load transfer. The shear pin 414 is designed to fail under a predetermined shear load that corresponds to an axial load transmitted by the driver 402. The axial load can be, for example, about 600 lbs for the modular hip implant 100 illustrated in FIG. 1, although other loads can be also selected. Referring to FIG. 19, the shear pin includes a notch 418, that causes the shear pin to break in a predictable manner providing a characteristic feedback to the surgeon during implantation. The shear pin 414 is disposable and can be provided in sterile packaging for convenience. The installation tool 400 and the shear pin 414 can be made of metal, such as a titanium alloy, Ti-6Al-4V, for example.

Figure 20:
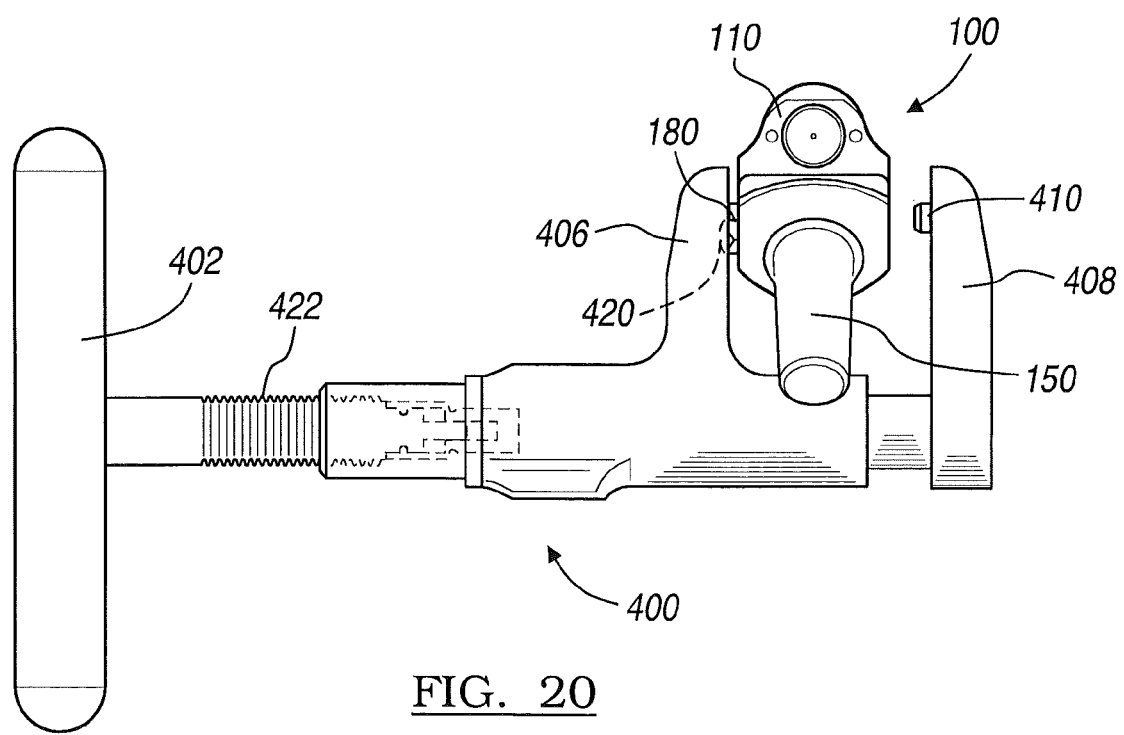
FIG. 20 is a top perspective view of the installation tool of FIG. 15 shown in preparation for use with a modular hip implant according to the present teachings.

The installation tool 400 is used to complete the installation of the key 180 after the femoral stem 110 and the neck component 150 are assembled, as shown in FIG. 2. The key 180 is first inserted manually into the keyway 170 to keep the components of the modular hip implant 100 together while the installation tool 400 is attached to the implant 100, as shown in FIG. 20. At this point, the key 180 is not yet fully wedged in the tapered keyway 170. The first and second jaws 406, 408 of the installation tool 400 are pulled apart against the spring action to receive the implant 100 therebetween, and then released, clamping onto the implant 100. While mounting the installation tool 400 on the implant 100, the first and second jaws 406, 408 are held such that a peg 410 on the second jaw 408 is received in one of two slots 181 that are shaped to mate with the peg 410. A reverse peg/slot arrangement can also be used (i.e., the peg on the implant and slot on the jaw). It is to be understood that the neck component 150 includes a pair of slots 181, one on each side of the neck component 150. The slot 181 illustrated in FIG. 17 is used with a removal tool for removing the key 180. The other slot 181 (not shown) receives the peg 410 and prevents rotation of the neck component 150 during installation of the key 180. The first jaw 406 includes a depression 420 shaped to mate with a corresponding surface of the partially-inserted key, as illustrated in FIG. 20. With the installation tool 400 engaging the implant 100, the driver 402 is rotated causing the first and second jaws 406, 408 to move closer to each other, such that the first jaw 406 pushes the protruding key 180 into the tapered keyway 170, wedging the key 180 into the keyway 170, thereby locking the implant 100. To avoid overloading of the implant 100, the shear pin 414 fractures in a controllable manner at the notch 418 when the axial load required for full wedging of the key 180 is reached.

It will be appreciated that the key 180 can be extracted using a removal tool that operates to push the key 180 out of the keyway 170. The removal tool (not shown) can be similar to the installation tool 400, and can include two jaws for holding the implant, and an optional shear pin.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A modular hip joint implant comprising:
   a femoral stem having a proximal surface defining a dovetail groove having first and second female wings; and
   a neck component having a distal surface defining a semi-dovetail projection engaging the dovetail groove, the projection including a single male wing mating with the first female wing.

2. The modular hip joint implant of claim 1, wherein the projection includes a planar surface providing a wall for a keyway defined between the second female wing of the dovetail groove and the neck component.

3. The modular hip joint implant of claim 2, wherein the planar surface forms an angle with a base surface of the dovetail groove.

4. The modular hip joint implant of claim 3, wherein the angle deviates from the perpendicular to the base surface by about 10°.

5. The modular hip joint implant of claim 2, wherein the planar surface is tapered in an anterior-posterior direction.

6. The modular hip joint implant of claim 2, further including a key insertable in the keyway.

7. The modular hip joint implant of claim 2, further including a key conforming with the keyway.

8. The modular hip joint implant of claim 2, wherein the key defines another male wing mating with the second female wing of the dovetail groove.

9. The modular hip joint implant of claim 1, wherein the dovetail groove has a bottom surface that defines a slot mating with a keel defined on the neck projection.

10. The modular hip joint implant of claim 1, wherein the dovetail groove has a bottom surface that defines two slots, one of which is selectively mating with a keel defined on the neck projection.

11. A modular hip joint implant comprising:
    a femoral stem implantable in a femur, the femoral stem having a proximal surface defining a dovetail groove having a base surface with first and second female wings and a first recessed slot formed on the base surface between the first and second wings; and a neck component having a distal surface defining a semi-dovetail projection and a keel extending from the projection, the keel slidably received in the first recessed slot and the projection slidably interlocking with the dovetail groove.

12. The modular hip joint implant of claim 11, wherein each female wing is selected from the group consisting of two-sided, arcuate, polygonal, rectangular and curved end grooves.

13. The modular hip joint implant of claim 11, further comprising a femoral head modularly coupled to the neck component.

14. The modular hip joint implant of claim 13, further comprising a stem extension modularly coupled to the femoral stem.

15. The modular hip joint implant of claim 11, further comprising an acetabular cup articulating with the femoral head.

16. The modular hip joint implant of claim 11, wherein the semi-dovetail projection includes a single male wing corresponding to the first female wing such that a keyway is defined between the second female wing and the neck component.

17. The modular hip joint implant of claim 11, further comprising a second recessed slot on the base surface for selectively receiving the keel of the neck component.

18. The modular hip joint implant of claim 17, wherein one of the first and second slots extends to an anterior surface of the femoral stem component and the other of the first and second slots extends to a posterior surface of the femoral stem component.

19. A modular hip joint implant comprising:

a femoral stem implantable in a femur, the femoral stem having a proximal surface defining a dovetail groove having a base surface with first and second female wings and first and second recessed slots formed on the base surface between the first and second wings and extending in a posterior anterior direction; and a neck component having a distal surface defining a semi-dovetail projection and a keel extending from the projection, the keel slidably received selectively in one of the first and second recessed slots and the projection slidably interlocking with the dovetail groove.

20. The modular hip joint implant of claim 19, wherein the semi-dovetail projection includes a single male wing corresponding to the first female wing such that a keyway is defined between the second female wing and the neck component.

* * * * *